United States Patent
Beacham (10) Patent No.: US 11,512,998 B2
(45) Date of Patent: Nov. 29, 2022

(54) SYSTEMS AND METHOD FOR AN AIR FLOW SENSOR IN A MEDICAL GAS FLOW DEVICE

(71) Applicant: GE Precision Healthcare LLC, Milwaukee, WI (US)

(72) Inventor: Jimmie Autrey Beacham, West Allis, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 596 days.

(21) Appl. No.: 16/575,295

(22) Filed: Sep. 18, 2019

(65) Prior Publication Data

US 2021/0080311 A1    Mar. 18, 2021

(51) Int. Cl.
*G01F 25/10*    (2022.01)
*G01F 1/20*    (2006.01)
(Continued)

(52) U.S. Cl.
CPC ............. *G01F 25/10* (2022.01); *A61M 16/01* (2013.01); *A61M 16/024* (2017.08);
(Continued)

(58) Field of Classification Search
CPC .......... G01F 25/10; G01F 25/15; G01F 25/11; G01F 25/12; G01F 25/13; G01F 25/14; G01F 25/17; G01F 1/206; G01F 1/20; G01F 1/203; G01F 1/22; G01F 1/24; G01F 1/26; G01F 1/28; G01F 1/34; G01F 1/36; G01F 1/363; G01F 1/366; G01F 1/50; G01F 1/05; G01F 1/053; G01F 1/056; G01F 1/06; G01F 1/08; A61M 16/021; A61M 16/022; A61M 16/024; A61M 16/026; A61M 2016/0027; A61M 2016/003; A61M 2016/0033; A61M 2016/0036;
(Continued)

(56) References Cited

U.S. PATENT DOCUMENTS

| | | | | |
|---|---|---|---|---|
| 5,038,621 A | * | 8/1991 | Stupecky | G01F 1/42 600/538 |
| 2004/0094157 A1 | * | 5/2004 | Dantanarayana | A61M 16/0816 128/207.12 |

(Continued)

FOREIGN PATENT DOCUMENTS

DE    3044219 A1 *   6/1982    ........... G01F 1/28

OTHER PUBLICATIONS

English Machine Translation of DE3044219A1 provided by Espacenet (Year: 1982).*

*Primary Examiner* — Joseph D. Boecker
*Assistant Examiner* — Brian T Khong
(74) *Attorney, Agent, or Firm* — McCoy Russell LLP (57) ABSTRACT

Systems and methods are provided for an air flow sensor assembly for a medical gas flow device. In one embodiment, a system for an air flow sensor assembly for a medical gas flow device includes an air flow passage having a flexible reed positioned therein, the flexible reed fixedly coupled to the air flow passage via an attachment point and having an edge smaller than an inner passage wall of the air flow passage, a planar surface of the flexible reed extending into a flow path of air flow through the air flow passage, and a strain gauge coupled to the planar surface of the flexible reed.

18 Claims, 5 Drawing Sheets

(51) Int. Cl.
*A61M 16/00* (2006.01)
*A61M 16/01* (2006.01)

(52) U.S. Cl.
CPC ....... *G01F 1/206* (2013.01); *A61M 2016/003* (2013.01); *A61M 2016/0027* (2013.01); *A61M 2230/40* (2013.01)

(58) Field of Classification Search
CPC .. A61M 2016/0039; A61M 2016/0042; G01L 27/007; G01L 27/005; G01P 5/02; G01P 5/04; G01P 5/06; A61B 5/0876
See application file for complete search history.

(56) References Cited

U.S. PATENT DOCUMENTS

| | | | | |
|---|---|---|---|---|
| 2014/0190579 | A1* | 7/2014 | Ding | G01F 15/005 137/487 |
| 2014/0277773 | A1* | 9/2014 | Goldschmidt | G01F 25/10 700/282 |
| 2019/0033896 | A1* | 1/2019 | Yasuda | G05B 19/416 |

* cited by examiner

SYSTEMS AND METHOD FOR AN AIR FLOW SENSOR IN A MEDICAL GAS FLOW DEVICE

FIELD

Embodiments of the subject matter disclosed herein relate to systems and methods for monitoring a gas flow through a medical device.

BACKGROUND

Some types of medical equipment, such as incubators and anesthesia machines, may include an advanced breathing system for moving breathable air into and out of a patient's lungs. The advanced breathing system may include a device for monitoring an air flow rate of the patient's breath. In some examples, the device may include a flexible reed that is perpendicular to the air flow path that is sensitive to changes in air flow through the device. For example, the flexible reed may bend bidirectionally, such as in a first direction during inhalation and a second, opposite direction during exhalation, in proportion to a mass flow rate of each breath. The device may include two pressure ports, one on each side of the flexible reed, to determine a pressure differential across the reed. This pressure differential may be used to determine the mass flow rate of the breath.

BRIEF DESCRIPTION

In one embodiment, a system for an air flow sensor assembly for a medical gas flow device includes an air flow passage having a flexible reed positioned therein, the flexible reed fixedly coupled to the air flow passage via an attachment point and having an edge smaller than an inner passage wall of the air flow passage, a planar surface of the flexible reed extending into a flow path of air flow through the air flow passage, and a strain gauge coupled to the planar surface of the flexible reed. In this way, an accuracy of an air flow rate determined via the air flow sensor assembly may be increased.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

The following description relates to various embodiments for an air flow sensor in a medical gas flow device, which may be an anesthesia machine, for example. Currently available air flow sensors may include a thin, flexible metal reed that is coupled perpendicular to an air flow path of the air flow sensor. The reed deflects proportionally to air flow through the air flow path, and a pressure across the reed (e.g., determined based on pressures measured upstream and downstream of the reed) may be used to determine a flow rate of the air flow. For example, the air flow sensor may be calibrated during manufacturing to determine a relationship between the pressure across the reed and the flow rate, which may be referenced to determine the flow rate of the air flow during medical gas flow device use. However, the relationship may change over time due to metal fatigue of the reed and other sources of calibration drift. Therefore, an accuracy of the flow rate determined based on the pressure across the reed may change over time.

Thus, according to embodiments disclosed herein, an air flow sensor is provided that includes a strain gauge printed on the reed. In the embodiments disclosed herein, the strain gauge directly measures a degree of deflection of the reed, which may be related to the flow rate of the air flow through the air flow sensor. According to embodiments disclosed herein, the degree of deflection may be used for self-calibration of the air flow sensor, thereby enabling higher accuracy flow rate determinations even as material properties of the reed change over time. In the embodiments disclosed herein, the air flow sensor may be used to determine the flow rate using two separate measurements, including determining a first air flow rate based on the pressure across the reed and determining a second air flow rate based on the deflection of the reed. A difference between the first air flow rate and the second air flow rate may be used to apply an adaptive correction to the calibration of the relationship between the pressure across the reed and the flow rate. The difference between the first air flow rate and the second air flow rate may also be used to identify degradation of the air flow sensor. Further, according to the embodiments disclosed herein, one or more of the first air flow rate and the second air flow rate may be used to control air flow through the medical gas flow device, such as by providing feedback for adjusting an amount of opening of a flow control valve.

The embodiments disclosed herein may provide several advantages. For example, the pressure across the reed is related to the deflection of the reed, which may be directly measured by the strain gauge. Thus, the strain gauge measurement may be used for continuous self-calibration of the relationship between air flow rate and the pressure across the reed across the product life of the air flow sensor. In this way, an accuracy of the air flow rate determination, and the resulting air flow control through the medical gas flow device, may be increased. Further, the strain gauge measurement may be used to identify degradation of the air flow sensor. In this way, the air flow sensor may be replaced responsive to degradation detection instead of at a fixed time duration. As a result, a service life of non-degraded air flow sensors may be extended, thereby reducing maintenance costs, while degraded air flow sensors may be quickly identified and repaired or replace, thereby increasing an accuracy of the air flow control through the medical gas flow device.

Figure 1:
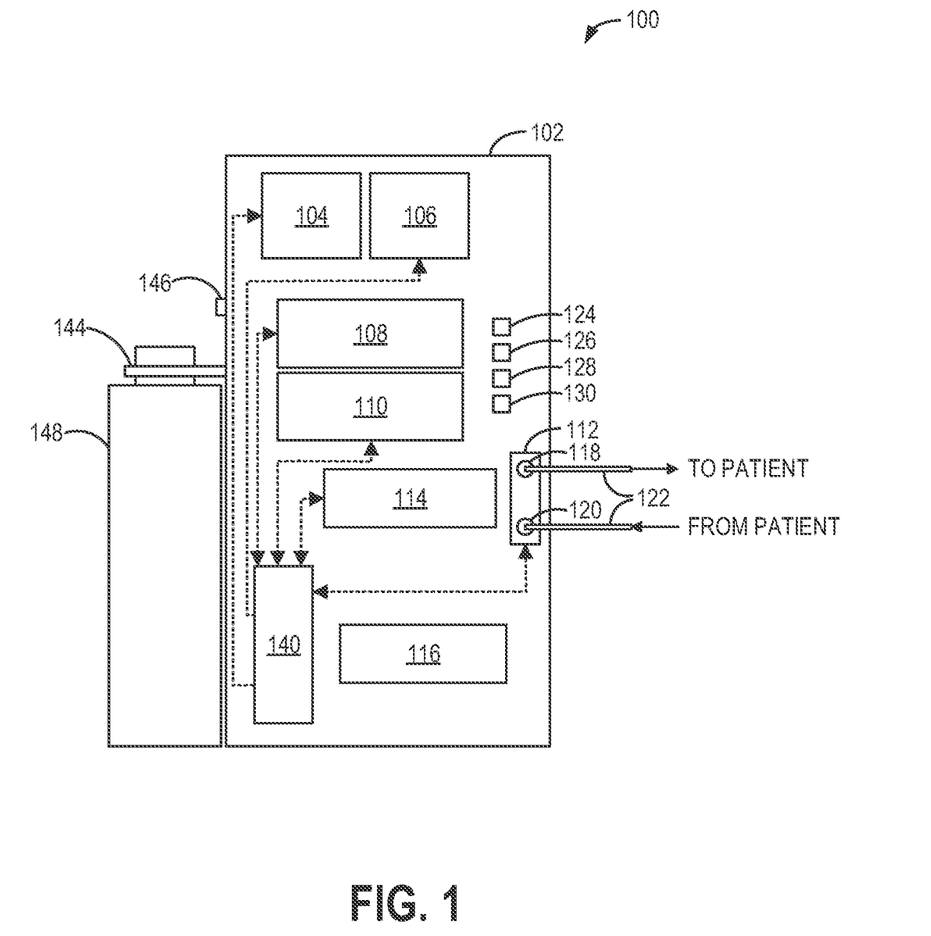
FIG. 1 schematically shows an exemplary embodiment of an anesthesia machine.
Figure 2:
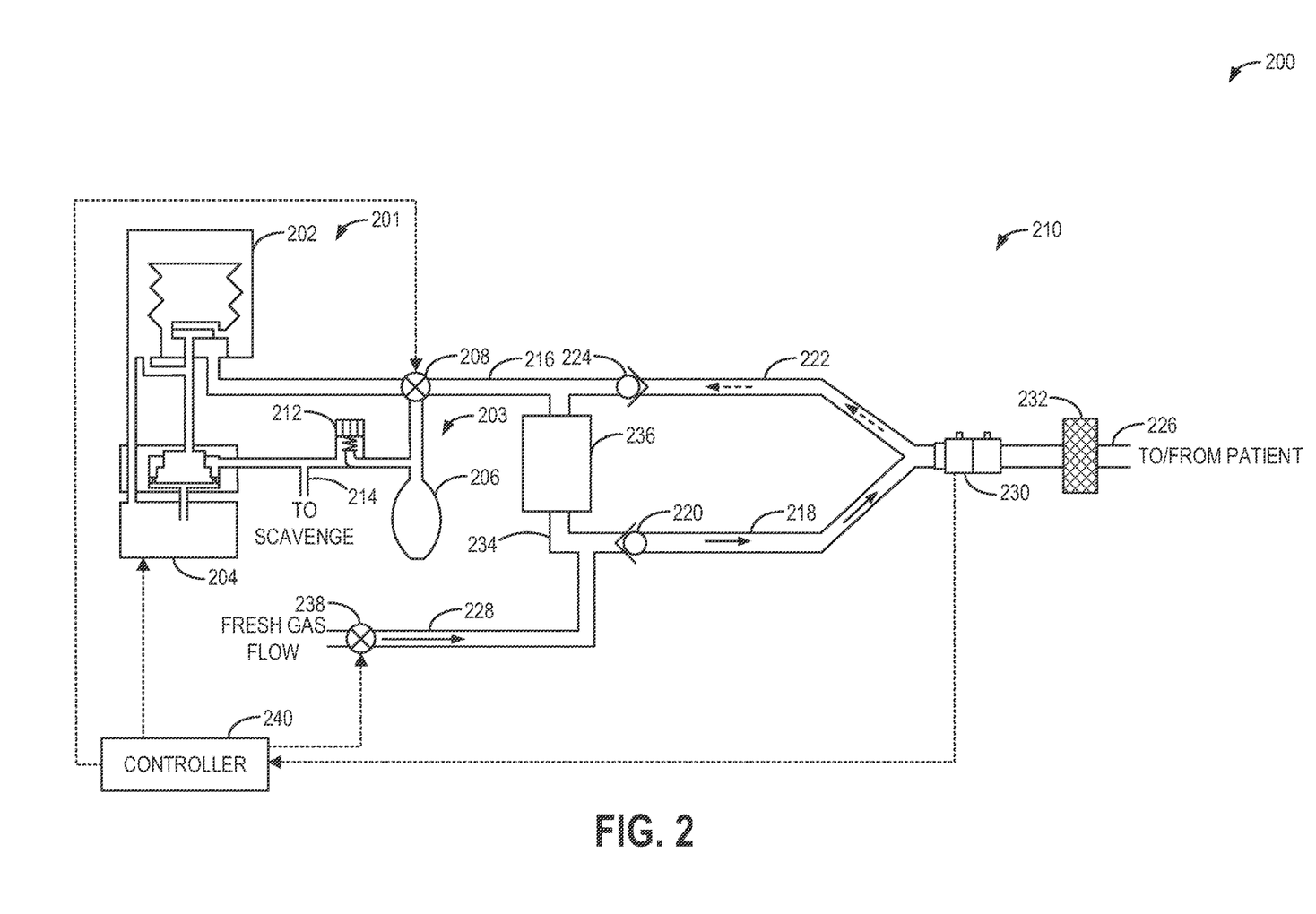
FIG. 2 schematically shows an exemplary embodiment of an advanced breathing system that may be included in an anesthesia machine.
Figure 3:
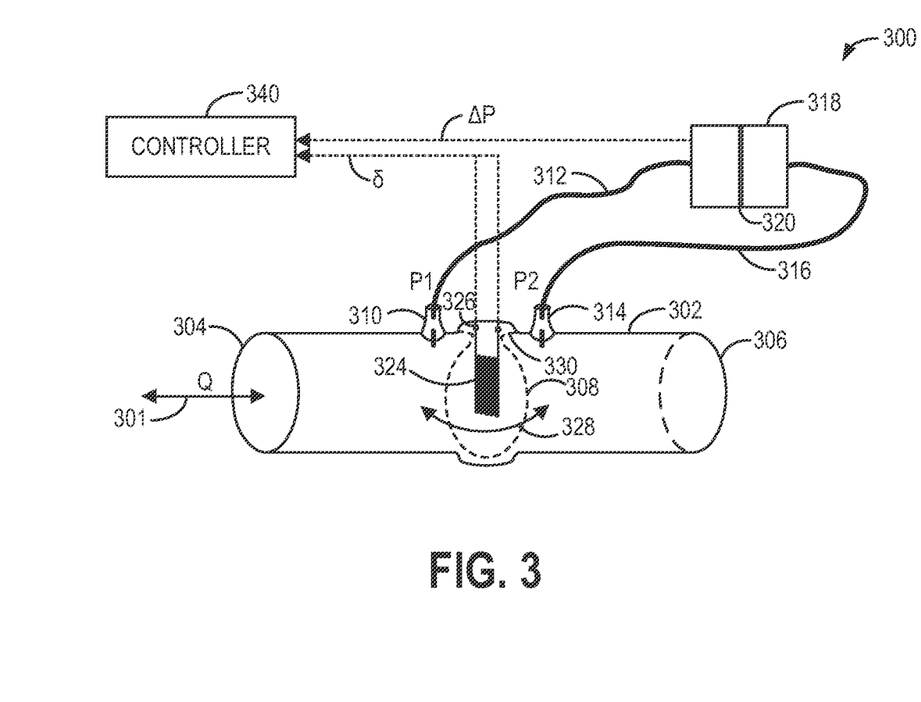
FIG. 3 schematically shows a perspective view of exemplary embodiment of an air flow sensor assembly that may be included in an advanced breathing system.
Figure 4:
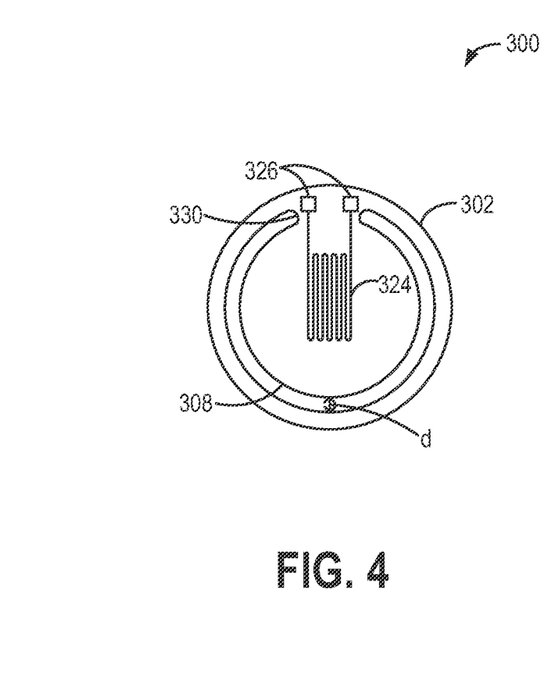
FIG. 4 schematically shows a partial cross-sectional view of the air flow sensor assembly of FIG. 3.

FIG. 1 schematically shows an exemplary embodiment of an anesthesia machine. FIG. 2 shows an exemplary embodiment of an advanced breathing system that may be included in the anesthesia machine of FIG. 1. FIG. 3 shows a perspective view of an exemplary embodiment of a strain gauged-enhanced air flow sensor assembly that may be included in the advanced breathing system of FIG. 2, while FIG. 4 shows a partial sectional view of the strain gauged-enhanced air flow sensor assembly. In particular, the strain gauged-enhanced air flow sensor assembly includes a strain gauge directly coupled to a flexible reed for measuring a deflection of the reed. The strain gauge may be coupled to a planar surface of the reed via additive manufacturing, such as according to the example method of FIG. 5. A controller may use both pressure and deflection measurements made by the strain gauged-enhanced air flow sensor assembly to determine an air flow rate through the air flow sensor assembly and control air flow through the advanced breathing system accordingly as well as to self-calibrate the air flow sensor assembly, such as according to the example method of FIG. 6.

Turning now to the figures, FIG. 1 schematically shows an example of a medical gas flow device. In particular, the medical gas flow device is an anesthesia machine 100. Anesthesia machine 100 includes a frame (or housing) 102. In some embodiments, frame 102 may be supported by casters, where the movement of the casters may be controlled (e.g., stopped) by one or more locks. In some examples, the frame 102 may be formed of a plastic material (e.g., polypropylene). In other examples, the frame 102 may be formed of a different type of material (e.g., metal, such as steel).

Anesthesia machine 100 also includes an anesthesia display device 104, a patient monitoring display device 106, a respiratory gas module 108, one or more patient monitoring modules, such as a patient monitoring module 110, an advanced breathing system (ABS) 112 (explained in more detail below), an anesthetic vaporizer 114, and an anesthetic agent storage bay 116. Anesthesia machine 100 may further include a main power indicator 124, a system activation switch 126 (which, in one example, permits gas flow when activated), an oxygen flush button 128, and an oxygen control 130. Anesthetic vaporizer 114 may vaporize the anesthetic agent and combine the vaporized anesthetic agent with one or more medical grade gases (e.g., oxygen, air, nitrous oxide, or combinations thereof), which may then be delivered to a patient.

Anesthesia machine 100 may additionally include an integrated suction, an auxiliary oxygen flow control, and various other components for providing and/or controlling a flow of the one or more medical grade gases to the patient. For example, anesthesia machine 100 includes one or more pipeline connections 146 to facilitate coupling of the anesthesia machine to pipeline gas sources. Additionally, anesthesia machine 100 includes a cylinder yoke 144, via which one or more gas-holding cylinders 148 may be coupled to the anesthesia machine. Thus, through the pipeline connection and/or cylinder connections, gas may be provided to the anesthesia machine, where the gas may include (but is not limited to) medical air, oxygen, nitrogen, and nitrous oxide. The gas that enters the anesthesia machine may mix with the vaporized anesthetic agent at the anesthetic vaporizer 114, as described above, before being supplied to a patient via the ABS 112. The anesthesia machine may also include a serial port, a collection bottle connection, a cylinder wrench storage area, and an anesthesia gas scavenging system.

In some embodiments, the ABS 112 may include an expiratory check valve at an expiratory port 120, an expiratory flow sensor at the expiratory port 120, an inspiratory check valve at an inspiratory port 118, an inspiratory flow sensor at the inspiratory port 118, an absorber canister, a manual bag port, a ventilator release, an adjustable pressure-limiting valve, a bag/vent switch, and a bellows assembly. When a patient breathing circuit is coupled to the ABS 112, breathing gases (e.g., air, oxygen, and/or nitrous oxide mixed with vaporized anesthetic agent) exit the anesthesia machine from the inspiratory port 118 and travel to the patient. Expiratory gases from the patient re-enter the anesthesia machine via the expiratory port 120, where carbon dioxide may be removed from the expiratory gases via the absorber canister. An example embodiment of an advanced breathing system will be described below with respect to FIG. 2.

During operation of the anesthetic vaporizer 114, an operator (e.g., an anesthesiologist) may adjust an amount of vaporized anesthetic agent that is supplied to the patient by adjusting a flow rate of gases from the gas source(s) (e.g., the pipeline gas supply) to the vaporizer. The flow rate of the gases from the gas source to the vaporizer may be adjusted by the operator via adjustment of one or more flow adjustment devices. For example, the flow adjustment devices may include analog and/or digital adjustment dials and/or other user input devices configured to actuate one or more flow control valves of anesthesia machine 100. In some embodiments, a first flow control valve may be positioned between the gas source(s) and the anesthetic vaporizer 114 and may be actuatable via the flow adjustment devices to a fully opened position, a fully closed position, and a plurality of positions between the fully opened position and the fully closed position.

Anesthesia machine 100 may additionally include one or more valves configured to bypass gases from the gas source(s) around the anesthetic vaporizer 114. The valves may enable a first portion of gases to flow directly from the gas source to the inspiratory port 118 and a second portion of gases to flow from the gas source through the anesthetic vaporizer 114 to mix with the vaporized anesthetic agents prior to flowing to the inspiratory port 118. By adjusting a ratio of the first portion of gases relative to the second portion of gases, the operator may control a concentration of vaporized anesthetic agent administered to the patient via the inspiratory port 118.

Further, the adjustments described above may be facilitated at least in part based on output from the respiratory gas module 108. The respiratory gas module 108 may be configured to measure various parameters of the gases exiting the vaporizer and/or being provided to the patient. For example, the respiratory gas module 108 may measure the concentrations of carbon dioxide, nitrous oxide, and the anesthetic agent provided to the patient. Further, the respiratory gas module 108 may measure respiration rate, minimum alveolar concentration, patient oxygen, and/or other parameters. The output from the respiratory gas module 108 may be displayed via a graphical user interface on a display device (e.g., the anesthesia display device 104 and/or the patient monitoring display device 106) and/or used by a controller to provide closed-loop feedback control of the amount of anesthesia provided to the patient.

The ABS 112 may optionally be coupled to a breathing circuit (not shown) via one or more tubes (e.g., gas passages) 122. The breathing circuit may be coupled between an airway of a patient (e.g., via a breathing mask positioned to enclose the mouth and/or nose of the patient or a tracheal intubation tube) and the inspiratory port 118 and the expiratory port 120. Gases (e.g., the one or more medical gases, or a mixture of the one or more medical gases and vaporized anesthetic agent from the anesthetic vaporizer 114) may flow from the inspiratory port 118, through the breathing circuit, and into the airway of the patient, where the gases are absorbed by the lungs of the patient. By adjusting the concentration of vaporized anesthetic agent in the gases as described above, the operator may adjust a degree to which the patient is anesthetized.

During conditions in which the breathing circuit is coupled to the airway, the anesthetic agent and/or fresh gas (without the anesthetic agent) may flow into the airway of the patient (e.g., through inhalation) via the inspiratory port 118 and the inspiratory check valve. As an example, the inspiratory check valve may open automatically (e.g., without input or adjustment by the operator) in response to inhalation by the patient and may close automatically in response to exhalation by the patient. Similarly, the expiratory check valve may open automatically in response to exhalation by the patient and may close automatically in response to inhalation by the patient.

In some embodiments, the operator may additionally or alternatively control one or more operating parameters of the anesthesia machine 100 via an electronic controller 140 of the anesthesia machine 100. Controller 140 includes a processor operatively connected to a memory. The memory may be a non-transitory computer-readable medium and may be configured to store computer executable code (e.g., instructions) to be processed by the processor in order to execute one or more routines, such as those described herein. The memory may also be configured to store data received by the processor. Controller 140 may be communicatively coupled (e.g., via wired or wireless connections) to one or more external or remote computing devices, such as a hospital computing system, and may be configured to send and receive various information, such as electronic medical record information, procedure information, and so forth. Controller 140 may also be electronically coupled to various other components of the anesthesia machine 100, such as the anesthetic vaporizer 114, the ABS 112, the respiratory gas module 108, the anesthesia display device 104, and the patient monitoring display device 106.

The controller 140 receives signals from the various sensors of the anesthesia machine 100 and employs the various actuators of the anesthesia machine 100 to adjust operation of the anesthesia machine 100 based on the received signals and instructions stored on the memory of the controller. For example, the flow of gases to the inspiratory port 118 may be controlled via an input device (e.g., keyboard, touchscreen, etc.) coupled to the electronic controller of the anesthesia machine 100. The controller 140 may display operating parameters of the anesthesia machine 100 via the anesthesia display device 104 and/or the patient monitoring display device 106. The controller may receive signals (e.g., electrical signals) via the input device and may adjust operating parameters of the anesthesia machine 100 in response (e.g., responsive) to the received signals.

As one example, the operator may input a desired concentration of the anesthetic agent to be delivered to the patient. A corresponding valve position of one or more valves of the anesthesia machine (e.g., a position of one or more bypass valves, as described above) may be empirically determined and stored in a predetermined lookup table or function in a memory of the controller. For example, the controller may receive the desired concentration of the anesthetic agent via the input device and may determine an amount of opening of the one or more valves corresponding to the desired concentration of the anesthetic agent based on the lookup table, with the input being the concentration of the anesthetic agent and the output being the valve position of the one or more valves. The controller may transmit an electrical signal to an actuator of the one or more valves in order to adjust each of the one or more valves to the corresponding output valve position. In some examples, the controller may compare the desired flow rate of gases to a measured flow rate of gases, such as measured by the inspiratory flow sensor, for example.

Controller 140 is shown in FIG. 1 for illustrative purposes, and it is to be understood that controller 140 may be located in various locations within, around, and/or remote from anesthesia machine 100. As an example, controller 140 may include multiple devices/modules that may be distributed throughout anesthesia machine 100. As such, controller 140 may include a plurality of controllers at various locations within anesthesia machine 100. As another example, additionally or alternatively, controller 140 may include one or more devices/modules that are external to anesthesia machine 100, located proximate to (e.g., in a same room) or remote from (e.g., a remote server) anesthesia machine 100. In each example, the multiple devices/modules may be communicatively coupled through wired and/or wireless connections.

Next, FIG. 2 shows an exemplary embodiment of an advanced breathing system (ABS) 200. As one example, ABS 200 may be ABS 112 included in anesthesia machine 100 of FIG. 1. In other examples, ABS 200 may be included in another medical gas flow system, such as an incubator. Further, ABS 200 is one example configuration of an advanced breathing system, and other configurations are also possible that include at least one air flow sensor, as will be elaborated below.

ABS 200 includes two ventilation systems for providing gas (e.g., air, medical gases, and/or anesthetic agent) to a patient: an electronically operated ventilator 201 and a manually operated ventilator 203. Electronically operated ventilator 201 includes a bellows assembly 202 and a ventilator drive 204. Manually operated ventilator 203 includes a bag 206 and an adjustable pressure-limiting (APL) valve 212. A bag/ventilator switch 208 controls selection between the two ventilation systems. For example, when manually operated ventilator 203 (e.g., bag ventilation) is selected at the bag/ventilator switch 208, bag 206 and APL valve 212 are connected to a circle breathing system 210 via a bidirectional gas passage 216, while bellows assembly 202 and ventilator drive 204 are disconnected. Bag 206 may be manually compressed by an operator of ABS 200 to pump gas through circle breathing system 210. Further, waste gas from patient exhalation may exit circle breathing system 210 via APL valve 212 and may be directed to a scavenge system via a scavenge passage 214.

When electronically operated ventilator 201 is selected at the bag/ventilator switch 208, bag 206 and APL valve 212 are disconnected from bidirectional gas passage 216 and circle breathing system 210, and electronically operated ventilator 201 provides patient inspiration and expiration. For example, ventilator drive 204 may be electronically controlled by a controller 240 (which may be part of controller 140 of FIG. 1, for example) to pneumatically compress bellows within bellows assembly 202 at a predetermined, adjustable rate. In addition, waste gas may exit circle breathing system 210 via bellows assembly 202 and ventilator drive 204 and may be directed to the scavenge system via the same scavenge passage 214. The scavenge system may remove anesthetic agent so that it is not released into a treatment room (such as an operating theater, patient room, etc.).

Circle breathing system 210 includes a plurality of gas passages coupled to bidirectional gas passage 216, including an inspiratory passage 218 having an inspiratory check valve 220 coupled therein, an expiratory passage 222 having an expiratory check valve 224 coupled therein, and a patient delivery passage 226 having an air flow sensor 230 and a filter 232 coupled therein. Patient delivery passage 226 may deliver gas (e.g., air, medical gases, and or anesthetic agent) from the selected ventilation system to the patient during inhalation (e.g., via inspiratory passage 218 and inspiratory check valve 220) and may deliver waste gas from the patient to the scavenge system during exhalation (e.g., via expiratory passage 222 and expiratory check valve 224). Air flow sensor 230 (which may also be referred to herein as an air flow sensor assembly) may measure a flow rate through patient delivery passage 226 during both inhalation and exhalation. However, in other examples, separate inhalation flow sensors and exhalation flow sensors may be included, such as one air flow sensor coupled in inspiratory passage 218 and another air flow sensor coupled in expiratory passage 222. An example embodiment of an air flow sensor that may be included in ABS 200 will be described below with respect to FIGS. 3 and 4.

In the example shown in FIG. 2, a gas passage 234 couples inspiratory passage 218 to expiratory passage 222 and includes an absorber canister 236 coupled therein. That is, gas passage 234 is coupled to inspiratory passage 218 upstream of inspiratory check valve 220 and is coupled to expiratory passage 222 downstream of expiratory check valve 224. Inspiratory check valve 220 is a one-way valve that automatically opens in response to inhalation by the patient and closes automatically in response to exhalation by the patient. Inspiratory check valve 220 enables gas to flow from bidirectional gas passage 216 to patient delivery passage 226 (e.g., via gas passage 234 and inspiratory passage 218) and blocks (e.g., prevents) gas flow from patient delivery passage 226 to gas passage 234. Similarly, expiratory check valve 224 is a one-way valve that automatically opens in response to exhalation by the patient and closes automatically in response to inhalation by the patient. Expiratory check valve 224 enables gas to flow from patient delivery passage 226 to bidirectional gas passage 216 and blocks gas flow from bidirectional gas passage 216 to patient delivery passage 226 via expiratory passage 222. Thus, all gas that flows to the patient flows through inspiratory passage 218, and all gas that flows from the patient flows through expiratory passage 222.

Waste gas exhaled by the patient may flow back to the selected ventilation system (via patient delivery passage 226 and expiratory passage 222), where it may be recycled. A fresh gas inlet 228 is positioned between absorber canister 236 and inspiratory check valve 220 so that a flow of gas provided to the patient on inspiration may include a mixture of enriched fresh gas (e.g., from an anesthetic vaporizer, such as anesthetic vaporizer 114 of FIG. 1) and scrubbed gas returned from bag 206 or bellows assembly 202 (depending on the position of the bag/ventilator switch 208) via absorber canister 236. Absorber canister 236 removes carbon dioxide from the waste gas exhaled by the patient, for example.

Fresh gas inlet 228 may include one or more flow control valves, such as a valve 238, for adjusting an amount (e.g., flow rate or concentration) of enriched fresh gas that is provided to ABS 200, and therefore, to the patient. It may be understood that the enriched fresh gas may include one or more medical gases (e.g., oxygen, nitrogen, air, and nitrous oxide) with or without anesthetic agent (e.g., depending on whether or not the patient is anesthetized). For example, valve 238 may be an electronically controlled, continuously variable valve that may be actuated into a plurality of positions between fully open and fully closed responsive to a command signal received from controller 240. As valve 238 is actuated to a further open position, enriched fresh gas flow through fresh gas inlet 228 increases, and as valve 238 is actuated to a further closed position, enriched fresh gas flow through fresh gas inlet 228 decreases. In some examples, controller 240 may adjust the position of valve 238 based on feedback received from air flow sensor 230, as will be elaborated herein with respect to FIG. 6.

ABS 200 may include additional valves, sensors, and gas inlets that are not shown in FIG. 2, such as various pressure relief and/or regulatory valves, pressure sensors, concentration sensors, and alternative fresh gas and/or oxygen inlets without departing from the scope of this disclosure. Thus, FIG. 2 may be understood to illustrate one embodiment of an example advanced breathing system that may provide mechanical ventilation to a patient.

Next, FIGS. 3 and 4 show an example embodiment of an air flow sensor assembly 300. Air flow sensor assembly 300 may be included in an advanced breathing system, such as ABS 200 of FIG. 2. For example, air flow sensor assembly 300 may be air flow sensor 230 of FIG. 2 and may be positioned to receive both inhalation and exhalation gases flowing to and from a patient, respectively. In particular, FIG. 3 shows a perspective view of air flow sensor assembly 300, whereas FIG. 4 shows a partial cross-sectional view of air flow sensor assembly 300. FIGS. 3 and 4 will be described collectively, with like components numbered the same. Further, it may be understood that FIGS. 3 and 4 are two-dimensional representations of three-dimensional objects having depth, width, and height.

As particularly illustrated in FIG. 3, air flow sensor assembly 300 includes a passage 302 having a first opening 304 and a second opening 306. Gases may flow through passage 302 in opposite directions during inhalation and exhalation, as represented by an arrow 301. As an illustrative example, gases may enter passage 302 via first opening 304 and exit passage 302 via second opening 306 during inhalation. Conversely, during exhalation, gases may enter passage 302 via second opening 306 and exit passage 302 via first opening 304.

Air flow sensor assembly 300 further includes a reed 308 that extends within passage 302, perpendicular to the gas flow path (e.g., arrow 301), and a differential pressure transducer 318 configured to measure a pressure difference across reed 308. Reed 308 creates a variable orifice within passage 302, as will be elaborated below, and may be comprised of a thin (e.g., ~100 μm) flexible metal (such as titanium, steel, etc.), for example. A first pressure port 310 is positioned on a first side of reed 308, between first opening 304 and reed 308, and is coupled to differential pressure transducer 318 via a first hose 312. A second pressure port 314 is positioned on a second side of reed 308, between second opening 306 and reed 308, and is coupled to differential pressure transducer 318 via a second hose 316. Differential pressure transducer 318 includes a pressure-sensitive disc 320, such as a piezo ceramic disc or a diaphragm, between first hose 312 and second hose 316. Thus, first hose 312 fluidically couples an interior of passage 302 on the first side of flexible reed, having a first pressure P1, to differential pressure transducer 318 (e.g., to a first side of pressure-sensitive disc 320), and second hose 316 fluidically couples the interior of passage 302 on the second side of flexible reed, having a second pressure P2, to differential pressure transducer 318 (e.g., to a second side of pressure-sensitive disc 320). Pressure-sensitive disc 320 may generate a voltage proportional to a delta (e.g., differential) pressure ($\Delta P$) across reed 308, which corresponds to the pressure difference between P1 and P2. The signal $\Delta P$ may be output to a controller 340 communicatively coupled to differential pressure transducer 318. Controller 340 may be a part of or may be communicatively coupled to one or both of controller 240 of FIG. 2 and controller 140 of FIG. 1, for example. However, in other examples, two pressure sensors may be used instead of the single differential pressure transducer 318, such as a first pressure sensor coupled to first hose 312 and a second pressure sensor coupled to second hose 316, and the pressure measurements from the two pressure sensors may be used to determine the pressure across reed 308. Further, it may be understood that first pressure port 310 upstream of reed 308 when gas flows through passage 302 from first opening 304 to second opening 306, and first pressure port 310 is downstream of reed 308 when gas flows through passage 302 from second opening 306 to first opening 304.

As mentioned above, reed 308 creates a variable orifice within passage 302. The variable orifice occurs due to a change in a distance d, illustrated in FIG. 4, between a perimeter edge of reed 308 and an inner surface (e.g., wall) of passage 302 that is caused by a deflection of reed 308 due to air flow through passage 302. Reed 308 is shown in a neutral position in FIGS. 3 and 4, in which reed 308 is planar and unbent. As shown by an arrow 328 in FIG. 3, reed 308 may deflect bidirectionally (e.g., toward first opening 304, or toward second opening 306) from the neutral, perpendicular position based on the direction of the air flow though passage 302. Further, reed 308 is coupled to passage 302 at an attachment point 330. Attachment point 330 may anchor reed 308 to passage 302. For example, as shown in FIGS. 3 and 4, attachment point 330 may be a neck-shaped region or portion of reed 308 that fixedly couples a body of reed 308 to passage 302. While attachment point 330 is coupled to (e.g., welded or joined to) passage 302, the body of reed 308 is spaced apart from the inner surface of passage 302. For example, the edge of reed 308 is smaller than (e.g., has a smaller diameter and circumference than) the inner surface of passage 302. The body of reed 308 may be disc-shaped, as shown, although other geometries are also possible (e.g., elliptical, square) that may also create a variable orifice as reed 308 deflects from the neutral position.

During the deflection, at least a portion of reed 308 is no longer planar and no longer perpendicular to the flow path (arrow 301). A portion of reed 308 farthest from attachment point 330 may deflect the most (e.g., to the greatest degree), with the deflection decreasing as the distance from attachment point 330 decreases. For example, attachment point 330 may remain approximately planar. Thus, the change in the distance d may vary around the perimeter of reed 308. Further, an angle (e.g., degree) of deflection from the neutral position, $\delta$, is proportional to an air (e.g., gas) flow rate through passage 302. As an example, as the air flow rate of gases entering passage 302 via first opening 304 and exiting passage 302 via second opening 306 increases, reed 308 may deflect toward second opening 306 by a larger amount. As another example, as the air flow rate of gases entering passage 302 via second opening 306 and exiting passage 302 via first opening 304 increases, reed 308 may deflect toward first opening 304 by a larger amount. A larger deflection produces a larger change in the distance d (e.g., a larger orifice), and a smaller deflection produces a smaller change in the distance d (e.g., a smaller orifice). Thus, the flexibility of reed 308 is sensitive to changes in air flow through passage 302. Further, the changing orifice results in a change in the delta pressure measured by differential pressure transducer 318. For example, as the deflection increases and the orifice increases, the delta pressure decreases, and as the deflection decreases and the orifice decreases, the delta pressure increases.

The relationship between the air flow rate and the delta pressure may be used by controller 340 to determine the air flow rate through passage 302 based on the signal $\Delta P$ output by differential pressure transducer 318. For example, air flow sensor assembly 300 may be calibrated during manufacture by measuring the resulting $\Delta P$ signal for a wide range of known air flow rates. The resulting calibrated relationship between $\Delta P$ and the air flow rate may be stored by controller 340 in non-transitory memory, such as in a look-up table, function, or graph. Thus, during use, controller 340 may input a measured $\Delta P$ into the calibrated look-up table, function, or graph, which may output the corresponding air flow rate. In one example, controller 340 (or another controller in electronic communication with controller 340) may use the resulting air flow rate to control valve adjustments in an advanced breathing system (e.g., valve 238 of ABS 200 of FIG. 2), as will be elaborated with respect to FIG. 6.

However, the relationship between the air flow rate and the deflection of reed 308, and thus the pressure difference across reed 308, may change over time, such as due to metal fatigue or other calibration drifts. Thus, air flow sensor assembly 300 further includes a strain gauge 324 positioned on reed 308. As will be further described below with respect to FIG. 5, strain gauge 324 may be printed directly on reed 308 during manufacture. In some examples, strain gauge 324 is printed on one planar surface (e.g., one side) of reed 308, while in other examples, one strain gauge 324 is printed on each planar surface (e.g., both sides) of reed 308. Strain gauge 324 is comprised of a thin, conductive strip in a zig-zag pattern of parallel lines. A length of strain gauge 324 (e.g., the longer, vertical dimension) is oriented perpendicular to the direction of flow (arrow 301) through passage 302.

The bending action of reed 308 during deflection causes strain on reed 308. Strain gauge 324 may measure an amount of strain in reed 308, which may be translated into the angle of deflection ($\delta$). For example, in the orientation illustrated in FIG. 3, strain gauge 324 compresses when reed 308 deflects toward first opening 304, and strain gauge 324 elongates when reed 308 deflects toward second opening 306. The change in strain gauge geometry that occurs during the mechanical compression or elongation changes a resistance between contact pads 326, positioned at attachment point 330. Strain gauge 324 may output a $\delta$ signal regarding the angle of deflection to controller 340 via contact pads 326.

Air flow sensor assembly 300 may be additionally calibrated during manufacture by measuring the resulting $\delta$ signal for a wide range of known air flow rates. The resulting calibrated relationship between $\delta$ and the air flow rate may be stored by controller 340 in non-transitory memory, such as in a look-up table, function, or graph. In some examples, during use, controller 340 may use the $\delta$ signal received from strain gauge 324 to calculate a second air flow rate through passage 302. For example, a flow rate Q may be calculated as a function of an area of first opening 304 (which may be the same as an area of second opening 306, for example), ΔP, and δ. The second air flow rate calculated based on the deflection of reed 308, as measured by strain gauge 324, may be used to compensate for non-linearity between ΔP and the air flow rate due to degradation and/or changes in reed 308 over time, thereby providing self-calibration of air flow sensor assembly 300 and increasing an accuracy of the resulting air flow rate. Further, the output from strain gauge 324 may help identify degradation that indicates sensor replacement, as will be further described with respect to FIG. 6.

Figure 5:
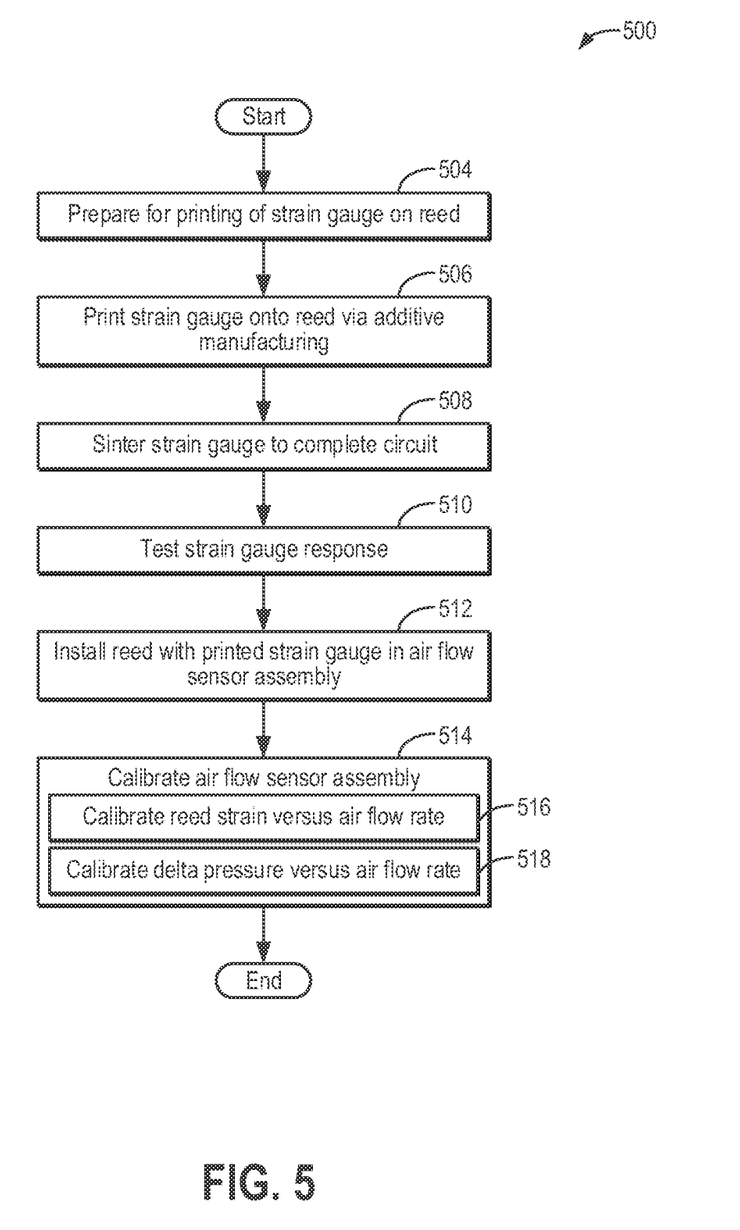
FIG. 5 is a flow chart illustrating an exemplary embodiment of a method for manufacturing a strain gauge-enhanced reed for an air flow sensor assembly.

Turning now to FIG. 5, a high-level flow chart of an example method 500 for manufacturing a strain gauge-enhanced air flow sensor assembly is shown. Method 500 may be carried out at least in part by an additive manufacturing device, which may be operatively/communicatively coupled to a printer-interfacing computing device. In particular, method 500 may be used to print a strain gauge on a reed, which may be reed 308 of FIGS. 3 and 4, for example, that is configured to be included in an air flow sensor assembly for use in a medical gas flow device, such as an advanced breathing system (e.g., ABS 200 of FIG. 2). By printing the strain gauge directly on the reed, the strain gauge may be customized to fit and effectively measure an amount of strain in the reed without affecting a function of the reed.

At 504, method 500 includes preparing for printing of the strain gauge on the reed. This may include physically preparing the reed, such as by inspecting the reed for material defects as well as cleaning a surface of the reed, as well as preparing the printer-interfacing computing device for printing. For example, the reed may be received from a supplier or manufactured (e.g., 3D printed) on-demand, prior to the strain gauge printing. The reed may be a thin (e.g., having a thickness ranging from 50-500 µm), flexible disc-like piece comprised of metal (such as titanium or steel). For example, the reed may be produced by the manufacturer according to thickness and diameter specifications and may include a base for attachment to the air flow sensor assembly (e.g., attachment point 330). For example, the method at 506 may include obtaining or generating a 3D model of the strain gauge to be printed on the reed. The model of the strain gauge may be a computer aided design (CAD) file, an additive manufacturing file (AMF), or other 3D modeling file. The 3D model of the strain gauge may be generated on the printer-interfacing computing device. In some examples, the 3D model may be generated entirely from operator instructions via the CAD or other program. In other embodiments, the 3D model may be generated at least in part from information received from a 3D scanner (e.g., a laser scanner) that may image a physical model of the strain gauge on the reed. The 3D model may define the dimensions of the strain gauge, a position of the strain gauge on the reed, a shape of the strain gauge, and material properties of the strain gauge, thereby fully representing, in a digital format, the final form of the strain gauge that will be produced on the reed. For example, as shown in FIGS. 3 and 4, the finished strain gauge may include a continuous conductive track having a zig-zag pattern with a plurality of bends between parallel sections and contact pads positioned on both terminal ends, and the 3D model may define the position of the bends and the contact pads with respect to each other and with respect to the base of the reed. Further, the dimensions of the strain gauge may be micrometer (µm) in scale. For example, the strain gauge may have a raised thickness from the reed ranging from 0.5-1.5 µm and may have a total width ranging from 10-15 µm across the reed.

At 506, method 500 includes printing the strain gauge onto the reed via the additive manufacturing (e.g., printing) device. The additive manufacturing device may utilize 3D printing or direct ink writing techniques, for example. Printing the strain gauge onto the reed may include, for example, first generating a plurality of 2D slices of the 3D model of the strain gauge. The slices may be generated on the printer-interfacing computing device and then the plurality of slices may be sent to the printing device as an STL file, or the 3D model of the strain gauge may be sent to the printing device, and the printing device may slice the 3D model into the plurality of slices to generate an STL file. In doing so, the 3D model is sliced into an appropriate number of horizontal layers of a suitable thickness. Alternatively, due to a size of the strain gauge, the strain gauge may be printed as a single layer.

Once the appropriate number of slices are generated, the printing device prints the first slice of the strain gauge on the reed. When the printing device prints from the STL file, the printing device creates or prints the strain gauge layer-by-layer on the reed. The printing device reads every slice (or 2D image) from the 3D model and proceeds to create the 3D strain gauge by laying down (or printing) successive layers of material on a planar surface of the reed until the entire strain gauge is created. Each of these layers may be a thinly sliced horizontal cross section of the eventually completed or printed 3D strain gauge.

The printing device may be a suitable device configured to print metal and/or other conductive materials. As one non-limiting example, the printing device may extrude a filament of a silver paste (or solution) from a print heat during printing, with the print head moved in both horizontal and vertical directions to complete or print each layer of the 3D model. Movement of the print head may be performed by a controlled mechanism that is operated by control software running on the printing device, e.g., a computer-aided manufacturing (CAM) software package adapted for use with the printing device. The reed may be held stationary, with its planar surface parallel to a horizontal plane, during the printing of each layer, and thus the print head may move relative to the stationary reed. The print head or reed is then moved vertically prior to starting the printing of the next layer, and this process may be repeated until all layers of the strain gauge have been printed.

At 508, method 500 includes sintering the strain gauge to complete a circuit. For example, the printing device may utilize selective laser melting (SLM) technology, direct metal laser sintering (DMLS) technology, or other suitable metal printing technology. In some examples, each individual layer may be sintered before the next (vertically higher) is printed. Additionally or alternatively, the entire strain gauge may be sintered after the printing is complete. The sintering may solidify the printed material and seal together layers of the strain gauge.

At 510, method 500 includes testing a response of the strain gauge. For example, a calibrated test amount of strain may be put on the reed, and the strain gauge response may be measured. As one example, the strain gauge may pass responsive to the strain gauge response (e.g., change in electrical resistance) being within an allowable range and may fail responsive to the strain gauge response being outside of the allowable range. As one illustrative example, if no strain gauge response is detected in response to mechanical compression or elongation caused by strain on the reed, such as due to a break in the circuit, the strain gauge may fail. In such an example, the circuit may be repaired to form a complete circuit, or the reed may be discarded.

At 512, method 500 includes installing the reed having the printed strain gauge in an air flow sensor assembly. For example, once the strain gauge response passes, the reed (including the strain gauge printed thereon) may be coupled to a passage of the air flow sensor assembly, perpendicular to a flow path through the passage and between two pressure measurement ports, such as schematically illustrated in FIG. 3. The two pressure measurement ports may be coupled to a differential pressure transducer via hoses, as also described above with respect to FIG. 3. Further, the strain gauge may be electronically coupled to a controller of the air flow sensor assembly (e.g., controller 340 of FIG. 3), such as by soldering leads to the contact pads.

At 514, method 500 includes calibrating the air flow sensor assembly. Calibrating the air flow sensor assembly includes both calibrating reed strain versus air flow rate, as indicated at 516, and calibrating delta pressure versus air flow rate, as indicated at 518. For example, calibrating the air flow sensor may include flowing gas through the air flow sensor assembly over a range of known air flow rates and measuring both the differential pressure transducer response and strain gauge response at each known air flow rate, either simultaneously or during a separate calibration procedure. Further, it may be understood that the calibrating may not be performed by the additive manufacturing device. For example, the calibrating may be performed at least partially by a calibration device and at least partially based on executable instructions stored in a memory of the controller of the air flow sensor assembly.

The delta pressure measured by the differential pressure sensor at each calibration point may be mapped against the air flow rate used during the measurement, such as in a first look-up table or graph. In some examples, the controller of the air flow sensor assembly may additionally determine a first mathematical function that defines the resulting relationship between the delta pressure and the air flow rate. The first look-up table, graph, and/or function may be stored in a memory of the controller so that the controller may reference the first look-up table, graph, and/or function to determine an unknown air flow rate based on a measured delta pressure.

Similarly, the strain (or change in electrical resistance) measured by the strain gauge at each calibration point may be mapped against the air flow rate used during the measurement, such as in a second look-up table or graph. In some examples, the controller of the air flow sensor assembly may additionally determine a second mathematical function that defines the resulting relationship between the strain and the air flow rate. The second look-up table, graph, and/or function may be stored in a memory of the controller so that the controller may reference the second look-up table, graph, and/or function to determine an unknown air flow rate based on a measured strain.

Further, the range of known air flow rates used during the calibration may encompass a range of air flow rates that are expected to be measured with the air flow sensor assembly after installation in an advanced breathing system, such as rates corresponding to infant breathing and rates corresponding to adult breathing, at least in some examples. By encompassing air flow rates to be measured within the calibration range, unknown air flow rates may be interpolated instead of extrapolated, thereby increasing an accuracy of the result. Method 500 may then end.

Thus, a strain gauge-enhanced reed may be manufactured and installed in an air flow sensor assembly that is further prepared for installation in a medical gas flow device. In particular, the air flow sensor assembly may be configured to measure a flow rate during patient inhalation and exhalation via two different measurements (e.g., a delta pressure measurement and a strain measurement).

Figure 6:
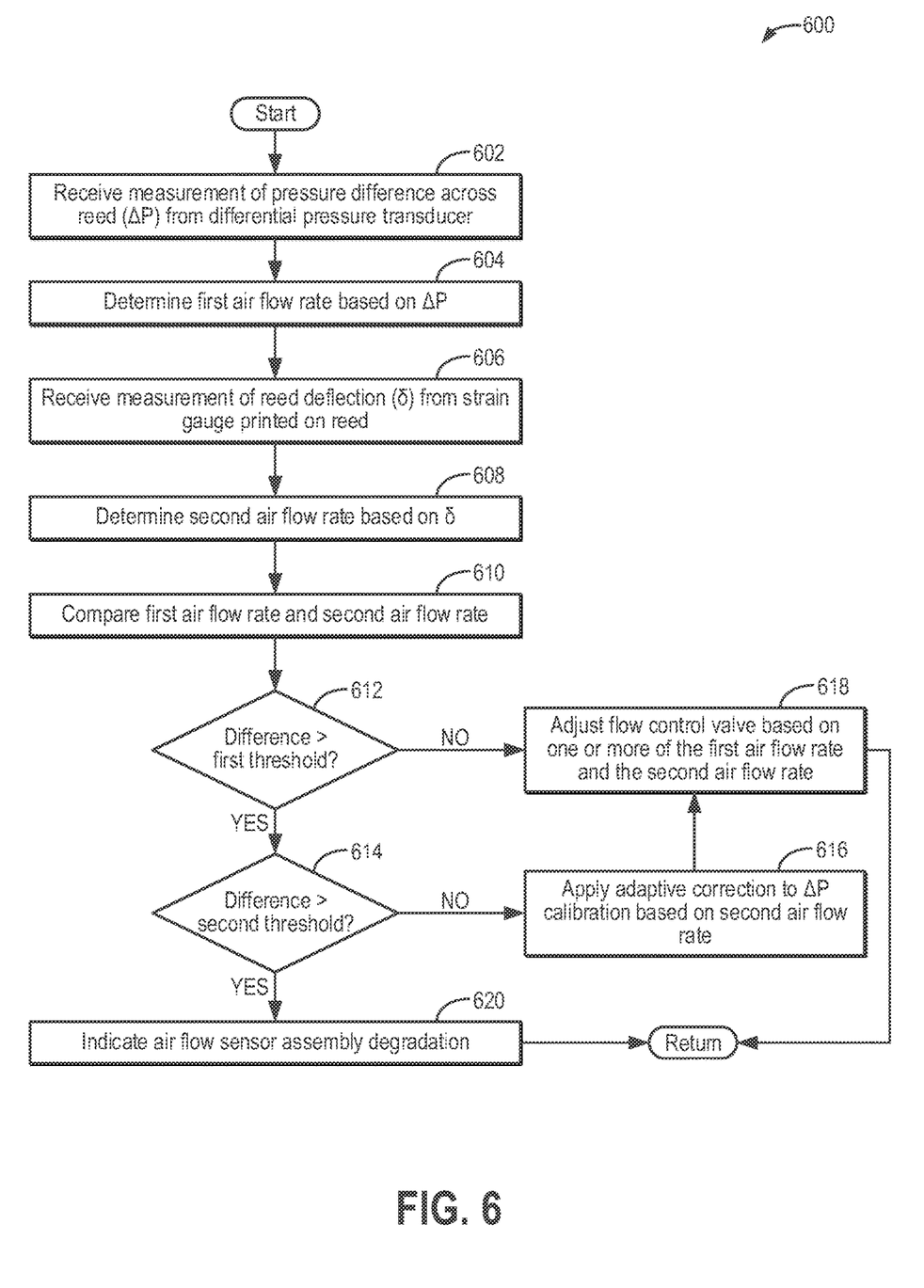
FIG. 6 is a flow chart illustrating an exemplary embodiment of a method for adjusting a medical gas flow based on feedback from a strain-gauged enhanced air flow sensor assembly.

Next, FIG. 6 shows an example method 600 for self-calibration and use of a strain gauge-enhanced air flow sensor, such as air flow sensor assembly 300 of FIGS. 3 and 4, for adjusting a medical gas flow to a patient breathing circuit (e.g., via an advanced breathing system, such as ABS 200 of FIG. 2). Method 600 may be executed by a controller, such as controller 240 of FIG. 2 and/or controller 340 of FIG. 3, according to instructions stored in a memory of the controller(s) and in conjunction with one or more inputs, such as inputs received from one or more sensors (e.g., differential pressure transducer 318 and strain gauge 324 introduced in FIG. 3). Further, the controller may employ actuators (e.g., valve 238 of FIG. 2) to adjust the medical gas flow according to the method described below.

At 602, method 600 includes receiving a measurement of a pressure difference ($\Delta P$) across a reed of the strain gauge-enhanced air flow sensor from the differential pressure transducer. As described above with respect to FIG. 3, the air flow sensor may include pressure ports on either side of the reed, with the reed serving as a variable orifice (e.g., restriction) that results in a varying pressure difference as gas flows through the strain gauge-enhanced air flow sensor. The differential pressure sensor, coupled to the pressure ports, may output a signal to the controller indicative of the pressure difference between the pressure ports.

At 604, method 600 includes determining a first air flow rate based on the pressure difference. For example, the controller may input the pressure difference signal received from the differential pressure sensor into a look-up table, function, or graph stored in memory, which may output the corresponding first air flow rate. In particular, the look-up table, function, or graph may define an empirically determined relationship between the pressure difference and the air flow rate determined during air flow sensor assembly calibration, as described above with respect to FIG. 5. The first air flow rate may include both a magnitude and a directionality, such as where the strain gauge-enhanced air flow sensor is positioned to measure a flow rate of both inhalation and exhalation gases.

At 606, method 600 includes receiving a measurement of a deflection of the reed ($\delta$) from a strain gauge printed on the reed. The deflection of the reed varies based on the air flow rate through the air flow sensor assembly, and the electrical resistance of the strain gauge varies based on the deflection of the reed. Therefore, the controller may receive a signal from the strain gauge indicative of the electrical resistance of the strain gauge, which represents the deflection of the reed. Further, measurement of the deflection of the reed may be time-aligned with the measurement of the pressure difference (e.g., as received at 602). For example, the controller may simultaneously receive the measurement of the pressure difference from the differential pressure transducer and the measurement of the deflection of the reed from the strain gauge. As another example, each measurement received from the differential pressure transducer and each measurement received from the strain gauge may be time-stamped to enable time alignment. As still another example, additionally or optionally, the differential pressure transducer and the strain gauge may use a clock and interrupt based-sampling to trigger synchronized measurements.

At 608, method 600 includes determining a second air flow rate based on the deflection of the reed. For example, the controller may input the deflection signal received from the strain gauge into a look-up table, function, or graph stored in memory, which may output the corresponding second air flow rate. In particular, the look-up table, function, or graph may define an empirically determined relationship between the deflection (e.g., angle of deflection) and the air flow rate determined during air flow sensor assembly calibration, as described above with respect to FIG. 5. Similar to the first air flow rate determined based on the pressure difference, the second air flow rate may also include both a magnitude and a directionality. Thus, the controller may determine the air flow rate two ways using the same air flow sensor assembly and two different output signals (e.g., the differential pressure transducer output and the strain gauge output).

At 610, method 600 includes comparing the first air flow rate and the second air flow rate. For example, the controller may directly compare the first air flow rate to the second air flow rate, such as by determining a difference between the first air flow rate and the second air flow rate. As another example, the controller may additionally or alternatively determine a percentage difference between the first air flow rate and the second air flow rate.

At 612, it is determined if the difference is greater than a first threshold. The first threshold may be a non-zero, pre-determined fixed value or may be a non-zero pre-determined percentage value that allows for slight discrepancies between the first air flow rate and the second air flow rate. For example, the first air flow rate and the second air flow rate may be in general agreement when the difference is less than the first threshold.

If the difference is not greater than the first threshold, method 600 proceeds to 618 and includes adjusting the flow control valve based on one or more of the first air flow rate and the second air flow rate. As an example, the flow control valve may adjust the medical gas flow rate provided to a patient, such as a flow of enriched fresh gas. One or more of the first air flow rate and the second air flow rate may provide feedback to the controller for maintaining the medical gas flow provided to a patient at a desired flow rate, which may be received from an operator. For example, in response to one or more of the first air flow rate and the second air flow rate being greater than the desired flow rate, the controller may actuate the flow control valve to a less open position, and in response to one or more of the first air flow rate and the second air flow rate being less than the desired air flow rate, the controller may actuate the flow control valve to a further open positon. As an example, the controller may input a difference between the measured air flow rate (e.g., one or more of the first air flow rate and the second air flow rate) into a look-up table, algorithm, or chart stored in memory, which may output the corresponding change to the flow control valve position. The controller may then generate a control signal to actuate the flow control valve to the determined position.

In one example, the controller may average the first air flow rate and the second air flow rate and then adjust the flow control valve position based on the average air flow rate. In other examples, the controller may select one of the first air flow rate and the second air flow rate for providing feedback for the flow control valve adjustment. In particular, the second air flow rate may be selected when the first air flow rate and the second air flow rate are not in agreement, as will be elaborated below.

Method 600 may then return. For example, method 600 may be repeated at a specified measurement frequency in order to update the air flow measurements, and thus update the flow control valve position, as the air flow measurements and/or the desired (e.g., commanded) air flow rate change. As one example, the differential pressure sensor and strain gauge measurements may be performed at a same frequency, enabling each (first) air flow rate determined based on the pressure difference across the reed to be evaluated against a corresponding (second) air flow rate determined based on the measurement of the reed deflection. As another example, the differential pressure sensor measurement may be performed more frequently than the strain gauge measurement, enabling a periodic evaluation of the air flow rate determined based on the pressure difference across the reed. Thus, in some examples, the $\Delta P$ measurement may be used to provide continuous feedback regarding the air flow rate for flow control valve adjustment while the $\delta$ measurement may provide continuous or discontinuous feedback regarding the differential pressure sensor calibration as well as the air flow rate.

Returning to 612, if the difference is greater than the first threshold, method 600 proceeds to 614 and includes determining if the difference is greater than a second threshold. The second threshold may be a non-zero, pre-determined fixed value or percentage value that is greater than the first threshold. For example, the second threshold may distinguish discrepancies between the first air flow rate and the second air flow rate due to calibration drift and air flow sensor wear that does not affect sensor function from discrepancies between the first air flow rate and the second air flow rate due to degradation that may affect sensor function.

If the difference is not greater than the second threshold (e.g., the difference is less than the second threshold), method 600 proceeds to 616 and includes applying an adaptive correction to the $\Delta P$ calibration based on the second air flow rate. That is, with the difference greater than the first threshold, the first air flow rate and the second air flow rate are not in agreement, but with the difference less than the second threshold, the difference may be corrected, such as by adjusting the calibrated relationship between the delta pressure across the reed and the air flow rate. As one example, the controller may learn the adaptive correction to apply by inputting the difference into a look-up table, function, or graph, which may output the adaptive correction to use for the $\Delta P$ calibration. For example, when applied, the adaptive correction may bring the first air flow rate determined using the $\Delta P$ measurement to be equal to the second air flow rate. In some examples, the adaptive correction may be stored in memory so that the controller may access and apply the adaptive correction during subsequent determinations of the first air flow rate.

Method 600 may then proceed to 618 to adjust the flow control valve based on one or more of the first air flow rate and the second air flow rate, as described above. In particular, the flow control valve may be adjusted based on the second air flow rate, as the second air flow rate has been used to re-calibrate the relationship between $\Delta P$ and the air flow rate. Upon repetition of method 600, the controller may continue to adjust the adaptive correction responsive to the difference remaining between the first threshold and the second threshold such that, in some examples, the adaptive correction term may be iteratively updated to increase an accuracy of the $\Delta P$ calibration. Further, in some examples, different adaptive correction terms may be learned and used for different flow rates (or flow rate ranges) to compensate for a non-linearity of the difference.

Returning to 614, if the difference is greater than the second threshold, method 600 proceeds to 620 and includes indicating air flow sensor assembly degradation. As one example, the controller may output an alert to a display or other human-machine interface that is operatively coupled to the controller. The alert may include an audible alarm and/or a visual (e.g., text or graphic-based) message, for example. The alert may specify that air flow sensor assembly degradation is present and may further include instructions for repair or replacement, for example. As another example, indicating air flow sensor degradation may additionally or alternatively include logging the degradation in memory, such as by storing a corresponding diagnostic code that may be accessed by a technician. Further, while air flow sensor assembly degradation is indicated, the flow control valve may be controlled in a feed-forward manner without feedback from the air flow sensor assembly. For example, the flow control valve may be adjusted to a pre-determined setting for a desired air flow that is stored in memory. Following 620, method 600 ends.

Thus, the systems and methods described herein provide for accurately determining an air (e.g., gas) flow rate in a medical gas flow device across time and across a wide range of flow rates. In particular, the medical gas flow device, such as an advanced breathing system included in an anesthesia machine or an incubator, includes a strain-gauge enhanced air flow sensor that enables air flow rate determination using two different measurements: a first air flow rate determination using a differential pressure measurement across a reed and a second air flow rate determination using a strain measurement of the reed. In this way, the two different air flow rates may be used for continuous self-calibration and degradation detection. As a result, a product life of the air flow sensor assembly may be extended while degradation may be detected throughout the product life, providing an alert when air flow sensor assembly replacement is indicated. A technical effect of printing a micro strain gauge directly onto a reed of an air flow sensor assembly of a medical gas flow device is that an air flow rate through the air flow sensor assembly can be determined via pressure-based and strain-based measurements, enabling self-calibration of the sensor and higher accuracy air flow rate determinations.

An example provides a system for an air flow sensor assembly for a medical gas flow device, comprising: an air flow passage having a flexible reed positioned therein, the flexible reed fixedly coupled to the air flow passage via an attachment point and having an edge smaller than an inner passage wall of the air flow passage, a planar surface of the flexible reed extending into a flow path of air flow through the air flow passage; and a strain gauge coupled to the planar surface of the flexible reed. In examples, the attachment point includes a neck-shaped region that anchors a disc-shaped body of the flexible reed to the air flow passage, and the disc-shaped body is spaced apart from the inner passage wall of the air flow passage. In one example, a length of the strain gauge extends from the attachment point to the disc-shaped body. In another example, the strain gauge includes contact pads positioned on the attachment point. In examples, a distance between the edge of the flexible reed and the inner passage wall of the air flow passage varies based on a rate of the air flow through the air flow passage.

In some examples, the system further includes a first port coupled to the air flow passage upstream of the flexible reed and a second port coupled to the air flow passage downstream of the flexible reed. As an example, the system further includes a differential pressure transducer fluidically coupled to a first side of the flexible reed via the first port and to a second side of the flexible reed via the second port.

In an example, the strain gauge is coupled to the planar surface of the flexible reed via additive manufacturing. In another example, the planar surface of the flexible reed is perpendicular to the flow path of air flow through the air flow passage.

Another example provides a method for a medical gas flow device, comprising: adjusting a flow control valve based on one or more of a first air flow rate and a second air flow rate responsive to a difference between the first air flow rate and the second air flow rate being less than a first threshold, the first air flow rate determined based on a pressure across a reed of an air flow sensor assembly and the second air flow rate determined based on a deflection of the reed. In examples, the method further includes applying an adaptive correction to a calibration for determining the first air flow rate responsive to the difference between the first air flow rate and the second air flow rate being greater than the first threshold and less than a second, higher threshold. As an example, the method further includes indicating degradation of the air flow sensor assembly responsive to the difference between the first air flow rate and the second air flow rate being greater than the second threshold. As another example, applying the adaptive correction to the calibration for determining the first air flow rate includes learning the adaptive correction based on the difference between the first air flow rate and the second air flow rate.

In examples, the reed extends into an air flow passage of the air flow pressure assembly, a body of the reed anchored to the air flow passage at a neck region and spaced apart from the air flow passage. As one example, the pressure across the reed is determined via output from a differential pressure transducer fluidically coupled to an interior of the air flow passage at a first pressure port upstream of the reed and a second pressure port downstream of the reed, and the deflection of the reed is determined via output from a strain gauge directly printed on a planar surface of the reed.

As an example, adjusting the flow control valve based on one or more of the first air flow rate and the second air flow rate includes further opening the flow control valve responsive to one or more of the first air flow rate and the second air flow rate being less than a desired air flow rate and further closing the flow control valve responsive to one or more of the first air flow rate and the second air flow rate being greater than the desired air flow rate.

An example provides a system for a medical gas flow device, comprising: one or more ventilation systems configured to be coupled to a patient breathing circuit via a patient delivery passage; an air flow sensor positioned in the patient delivery passage, the air flow sensor including a pressure transducer coupled across a reed and a strain gauge coupled to the reed; and a controller including instructions stored in non-transitory memory that, when executed, cause the controller to: determine a first air flow rate through the patient delivery passage based on an output from the pressure transducer; and correct the first air flow rate based on an output from the strain gauge.

In examples, to correct the first air flow rate based on the output from the strain gauge, the controller includes further instructions stored in non-transitory memory that, when executed, cause the controller to: determine a second air flow rate based on the output from the strain gauge, the output from the strain gauge time-aligned with the output from the pressure transducer; determine an adaptive correction based on a difference between the first air flow rate and the second air flow rate; and apply the adaptive correction to the output from the pressure transducer. As one example, the controller includes further instructions stored in non-transitory memory that, when executed, cause the controller to: indicate degradation of the air flow sensor responsive to the difference between the first air flow rate and the second air flow rate being greater than a threshold.

As an example, the system further comprises a fresh gas inlet coupled to the patient delivery passage, the fresh gas inlet including a flow control valve positioned therein, and the controller includes further instructions stored in non-transitory memory that, when executed, cause the controller to: adjust the flow control valve to a further open position responsive to the first air flow rate being less than a desired air flow rate; and adjust the flow control valve to a further closed position responsive to the first air flow rate being greater than the desired air flow rate.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for an air flow sensor assembly for a medical gas flow device, comprising:
    an air flow passage having a flexible reed positioned therein, the flexible reed fixedly coupled to the air flow passage via an attachment point and having an edge smaller than an inner passage wall of the air flow passage, a planar surface of the flexible reed extending into a flow path of air flow through the air flow passage;
    a strain gauge coupled to the planar surface of the flexible reed;
    a first port coupled to the air flow passage upstream of the flexible reed and a second port coupled to the air flow passage downstream of the flexible reed; and
    a differential pressure transducer fluidically coupled to a first side of the flexible reed via the first port and to a second side of the flexible reed via the second port.

2. The system of claim 1, wherein the attachment point includes a neck-shaped region that anchors a disc-shaped body of the flexible reed to the air flow passage, and the disc-shaped body is spaced apart from the inner passage wall of the air flow passage.

3. The system of claim 2, wherein a length of the strain gauge extends from the attachment point to the disc-shaped body.

4. The system of claim 3, wherein the strain gauge includes contact pads positioned on the attachment point.

5. The system of claim 1, wherein a distance between the edge of the flexible reed and the inner passage wall of the air flow passage varies based on a rate of the air flow through the air flow passage.

6. The system of claim 1, wherein the strain gauge is coupled to the planar surface of the flexible reed via additive manufacturing.

7. The system of claim 1, wherein the planar surface of the flexible reed is perpendicular to the flow path of air flow through the air flow passage.

8. A method for a medical gas flow device, comprising:
    adjusting, via a controller, a flow control valve based on one or more of a first air flow rate and a second air flow rate responsive to a difference between the first air flow rate and the second air flow rate being less than a first threshold, the first air flow rate determined by the controller based on a measured pressure across a reed of an air flow sensor assembly and the second air flow rate determined by the controller based on a deflection of the reed.

9. The method of claim 8, further comprising applying, via the controller, an adaptive correction to a calibration for determining the first air flow rate responsive to the difference between the first air flow rate and the second air flow rate being greater than the first threshold and less than a second, higher threshold.

10. The method of claim 9, further comprising indicating degradation of the air flow sensor assembly via the controller responsive to the difference between the first air flow rate and the second air flow rate being greater than the second threshold.

11. The method of claim 9, wherein applying, via the controller, the adaptive correction to the calibration for determining the first air flow rate includes the controller learning the adaptive correction based on the difference between the first air flow rate and the second air flow rate.

12. The method of claim 8, wherein the reed extends into an air flow passage of the air flow sensor assembly, a body of the reed anchored to the air flow passage at a neck region and spaced apart from the air flow passage.

13. The method of claim 12, wherein the measured pressure across the reed is determined via an output from a differential pressure transducer fluidically coupled to an interior of the air flow passage at a first pressure port upstream of the reed and a second pressure port downstream of the reed, and the deflection of the reed is determined via an output from a strain gauge directly printed on a planar surface of the reed.

14. The method of claim 8, wherein adjusting, via the controller, the flow control valve based on one or more of the first air flow rate and the second air flow rate includes further opening the flow control valve via the controller responsive to one or more of the first air flow rate and the second air flow rate being less than a desired air flow rate received by the controller from user input and further closing the flow control valve via the controller responsive to one or more of the first air flow rate and the second air flow rate being greater than the desired air flow rate.

15. A system for a medical gas flow device, comprising:
    one or more ventilation systems configured to be coupled to a patient breathing circuit via a patient delivery passage;

an air flow sensor positioned in the patient delivery passage, the air flow sensor including a pressure transducer coupled across a reed and a strain gauge coupled to the reed; and a controller including instructions stored in non-transitory memory that, when executed, cause the controller to:
determine a first air flow rate through the patient delivery passage based on an output from the pressure transducer; and
correct the first air flow rate based on an output from the strain gauge.

16. The system of claim 15, wherein to correct the first air flow rate based on the output from the strain gauge, the controller includes further instructions stored in non-transitory memory that, when executed, cause the controller to:
determine a second air flow rate based on the output from the strain gauge, the output from the strain gauge time-aligned with the output from the pressure transducer;
determine an adaptive correction based on a difference between the first air flow rate and the second air flow rate; and
apply the adaptive correction to the output from the pressure transducer.

17. The system of claim 16, wherein the controller includes further instructions stored in non-transitory memory that, when executed, cause the controller to:
indicate degradation of the air flow sensor responsive to the difference between the first air flow rate and the second air flow rate being greater than a threshold.

18. The system of claim 15, further comprising a fresh gas inlet coupled to the patient delivery passage, the fresh gas inlet including a flow control valve positioned therein, and wherein the controller includes further instructions stored in non-transitory memory that, when executed, cause the controller to:
adjust the flow control valve to a further open position responsive to the first air flow rate being less than a desired air flow rate; and
adjust the flow control valve to a further closed position responsive to the first air flow rate being greater than the desired air flow rate.

* * * * *